United States Patent [19]
Knowles et al.

[11] Patent Number: 5,656,206
[45] Date of Patent: Aug. 12, 1997

[54] SUBSTITUTED NAPHTHOPYRANS

[75] Inventors: David B. Knowles, Apollo; Barry Van Gemert, Murrysville; Anil Kumar, Pittsburgh, all of Pa.

[73] Assignee: Transitions Optical, Inc., Pinellas Park, Fla.

[21] Appl. No.: 490,190

[22] Filed: Jun. 14, 1995

[51] Int. Cl.$^6$ .......................... C08K 5/15; C07D 311/78; C07D 405/02; C02B 1/04; C02B 5/23

[52] U.S. Cl. .......................... 252/586; 549/389; 549/362; 549/331; 549/214; 549/60; 549/58; 549/48; 549/43; 548/525; 548/454; 548/440; 548/406; 548/364.4; 548/311.4; 546/196; 546/164; 546/14; 544/375; 544/150; 524/110; 524/109; 524/104; 524/99

[58] Field of Search .................... 549/389, 214, 549/43, 48, 58, 60, 331, 362; 548/406, 440, 454, 525, 364.4, 311.4; 546/196, 14, 164; 544/375, 150; 524/110, 109, 104, 99; 252/586

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/160 |
| 4,980,089 | 12/1990 | Heller | 252/586 |
| 4,994,208 | 2/1991 | McBain et al. | 252/586 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,384,077 | 1/1995 | Knowles | 252/586 |
| 5,405,958 | 4/1995 | Van Gemert | 544/71 |
| 5,411,679 | 5/1995 | Kumar | 252/586 |

FOREIGN PATENT DOCUMENTS

| | | |
|---|---|---|
| 7-41758 | 7/1995 | Japan . |
| 7-48363 | 7/1995 | Japan . |
| 7-48566 | 7/1995 | Japan . |
| 7-48567 | 7/1995 | Japan . |

OTHER PUBLICATIONS

*Friedel–Crafts and Related Reactions*, George A. Olah, Interscience Publishers, vol. 3 Chapter XXXI, pp. 1–8, 1964.

"Regioselective Friedel Crafts Acylation of 1,2,3,4–Tetrahydroquinoline and Related Nitrogen Heterocycles: Effects of NH Protective Groups and Ring Size", Ishihara, Y., et al., J. Chem. Soc., Perkin Trans. 1, pp. 3401–3406, 1992.

"Fast Fading Naphtho[1,2–b]pyran Photochromics", Research Disclosure, May 1994, pp. 267–268.

"Synthesis, Conformation, and Complexation Behavior of 2, 9,18,25–Tetraoxa [8,8](1,4)naphthalenophane", Adams, S.P., et al, J. Org. Chem., vol. 46, pp. 3474–3478, 1981. see Experimental Section on p. 3477 for discussion of Methyl 1,4–Dihydroxy–2–naphthoate.

*Organic Reactions*, vol. VI, John Wiley & Sons, Inc. Chapter 1, pp. 1–2 (1951).

Primary Examiner—Nicky Chan
Attorney, Agent, or Firm—Frank P. Mallak; Irwin M. Stein

[57] ABSTRACT

Described are novel reversible photochromic 2H-naphtho[1,2-b]pyran compounds, examples of which are compounds having certain substituents at the number 5 carbon atom of the naphtho portion of the naphthopyran and at the 2-position of the pyran ring. Certain substituents may also be present at the number 6, 7, 8, 9 or 10 carbon atoms of the naphtho portion of the naphthopyran. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(indoline) type compounds, are also described.

25 Claims, No Drawings

SUBSTITUTED NAPHTHOPYRANS

DESCRIPTION OF THE INVENTION

The present invention relates to certain novel naphthopyran compounds. More particularly, this invention relates to novel photochromic naphthopyran compounds and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinue, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl- 2H-naphtho[1,2-b]pyrans, which are reported to require unacceptably long periods of time to fade after activation.

U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1, 2-b]pyrans without the aforementioned additives ranges from several hours to many days to reach complete reversion. U.S. Pat. No. 4,818,096 discloses a blue coloring photochromic benzo- or naphthopyran having at the position alpha to the oxygen of the pyran ring a phenyl group having a nitrogen containing substituent in the ortho or para positions.

The present invention relates to novel substituted 2H-naphtho[1,2-b]pyran compounds which have been unexpectedly found to have an acceptable fade rate in addition to a high activated intensity and a high coloration rate. In particular, the use of certain substituents at the 5-position of the naphtho-portion of the naphthopyran compound increases the fade rate without the addition of acids or bases. In addition, these compounds have certain substituents at the 2-position of the pyran ring. Certain substituents may also be present at the number 6, 7, 8, 9 or 10 carbon atoms of the naphtho portion of the naphthopyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel 2H-naphtho[1,2-b]pyran compounds having an acceptable fade rate, high activated intensity and a high coloration rate may be prepared. These compounds may be described as naphthopyrans having certain substituents at the 2 position of the pyran ring and at the number 5 carbon atom of the naphtho- portion of the naphthopyran ring. Certain substituents may also be present at the 6, 7, 8, 9 or 10 carbon atoms of the naphtho portion of the naphthopyran ring. These compounds may be represented by the following graphic formula:

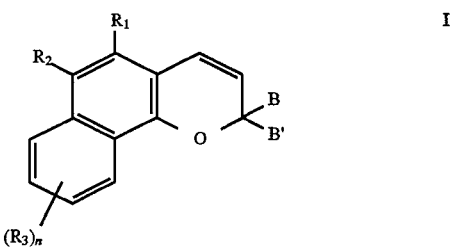

In graphic formula I, $R_1$ may be the group, —$CH_2X$ or —$C(O)Y$, X may be halogen, hydroxy, benzoyloxy, $C_1$–$C_6$ alkoxy, $C_2$–$C_6$ acyloxy, amino, $C_1$–$C_6$ mono-alkylamino, $C_1$–$C_6$ dialkylamino, i.e., di($C_1$–$C_6$) alkylamino, morpholino, piperidino, 1-indolinyl, pyrrolidyl, trimethylsilyloxy, or the group, —$OCH(R_{11})Z$; Y may be the group, —$OCH(R_{11})Z$ or an unsubstituted, mono-substituted, or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl; Z being —CN, —$CF_3$, halogen, —$C(O)R_{12}$, or $COOR_{12}$; $R_{11}$ may be hydrogen or $C_1$–$C_6$ alkyl; the heterocyclic ring substituents may be $C_1$–$C_6$ alkyl or $C_1$–$C_6$ alkoxy, and halogen may be chloro or fluoro.

Preferably, $R_1$ is the group, —$CH_2X$ or —$C(O)Y$, wherein X is hydroxy, $C_1$–$C_4$ alkoxy, or $C_2$–$C_4$ acyloxy, Y is the group, —$OCH(R_{11})Z$, or an unsubstituted or mono-substituted heterocyclic ring selected from the group consisting of 1-indolinyl, morpholino, piperidino, and 1-pyrrolidyl, wherein Z is —CN, —$C(O)R_{12}$, or —$COOR_{12}$, $R_{11}$ and $R_{12}$ are is hydrogen or $C_1$–$C_4$ alkyl; and the heterocyclic ring substituents are $C_1$–$C_4$ alkyl or $C_1$–$C_4$ alkoxy.

More preferably, $R_1$ is the group, —$CH_2X$, or —$C(O)Y$, wherein X is hydroxy, $C_1$–$C_4$ alkoxy, or $C_2$–$C_4$ acyloxy and Y is an unsubstituted or mono-substituted heterocyclic ring selected from the group consisting of 1-indolinyl, morpholino, and piperidino. Most preferably, $R_1$ is hydroxymethyl, acetoxymethyl, morpholinocarbonyl, or piperidinocarbonyl.

$R_2$ and each $R_3$ in graphic formula I may be hydrogen, $C_1$–$C_6$ alkyl, $C_3$–$C_7$ cycloalkyl, unsubstituted, mono-, di-, or tri-substituted phenyl, the group, —$OR_6$, wherein $R_6$ may be hydrogen, ($C_1$–$C_6$)alkyl, phenyl($C_1$–$C_3$)alkyl, mono-substituted phenyl($C_1$–$C_3$)alkyl, ($C_1$–$C_6$)alkoxy($C_2$–$C_4$) alkyl, $C_3$–$C_7$ cycloalkyl, mono($C_1$–$C_4$)alkyl substituted $C_3$–$C_7$ cycloalkyl, $C_1$–$C_6$ haloalkyl, allyl, the group, —CH($R_7$)W, wherein W may be —CN, —$CF_3$, halogen, —C(O)$R_7$, or —$COOR_7$, wherein $R_7$ may be hydrogen, $C_1$–$C_6$ alkyl, or ($C_1$–$C_6$)alkoxy($C_2$–$C_4$)alkyl, or $R_6$ may be the group, —C(O)T, wherein T may be hydrogen, $C_1$–$C_6$ alkyl, $C_1$–$C_6$ alkoxy, the substituted or unsubstituted aryl groups phenyl or naphthyl, phenoxy, $C_1$–$C_6$ mono-or di-alkyl substituted phenoxy, $C_1$–$C_6$ mono-or di-alkoxy substituted phenoxy, $C_1$–$C_6$ mono-or di- alkoxy substituted phenylamino, each of said phenyl or naphthyl substituents being $C_1$–$C_6$ alkyl, $C_1$–$C_6$ alkoxy or halogen, each of said halogen or halo substituents being chloro or fluoro, and n is selected from the integers 0, 1, 2, and 3.

Preferably, $R_2$ and each $R_3$ are hydrogen, $C_1$–$C_4$ alkyl, unsubstituted, mono-, di-, or tri-substituted phenyl, the group, —$OR_6$, wherein $R_6$ is $C_1$–$C_4$ alkyl or the group, —CH($R_7$)W, wherein W is —$COOR_7$, and $R_7$ is hydrogen or $C_1$–$C_4$ alkyl, the phenyl substituents are $C_1$–$C_4$ alkyl, $C_1$–$C_4$ alkoxy or fluoro and n is selected from the integers 0, 1 and 2.

More preferably, $R_2$ and each $R_3$ are hydrogen, $C_1$–$C_2$ alkyl, unsubstituted, mono-, di-, or tri-substituted phenyl, the group, —$OR_6$, wherein $R_6$ is $C_1$–$C_2$ alkyl or the group, —CH($R_7$)W, wherein W is —$COOR_7$, and $R_7$ is $C_1$–$C_2$ alkyl, the phenyl substituents are $C_1$–$C_2$ alkyl, $C_1$–$C_2$ alkoxy or fluoro, and n is selected from the integers 0, 1 and 2. Most preferably, $R_2$ and each $R_3$ are hydrogen, phenyl, methoxy, methyl or fluoro.

In graphic formula I, B and B' may each be selected from the group consisting of: (i) the unsubstituted, mono-, di-, and tri-substituted aryl groups phenyl and naphthyl; (ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl, and carbazolyl, the aryl and heterocyclic substituents being selected from the group consisting of hydroxy, amino, $C_1$–$C_6$ monoalkylamino, $C_1$–$C_6$ dialkylamino, morpholino, piperidino, 1-indolinyl, pyrrolidyl, 1-imidazolidyl, 2-imidazolin-1-yl, 2-pyrazolidyl, pyrazolinyl, 1-piperazinyl, $C_1$–$C_6$ alkyl, $C_1$–$C_6$ haloalkyl, $C_1$–$C_6$ alkoxy, mono($C_1$–$C_6$)alkoxy($C_1$–$C_4$)alkyl, acryloxy, methacryloxy, and halogen, wherein the halogen or (halo) group may be fluoro or chloro; (iii) the groups represented by the following graphic formulae II A and II B:

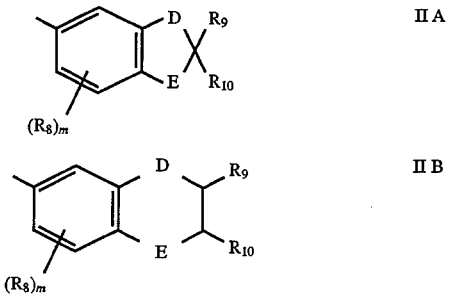

wherein D may be carbon or oxygen and E may be oxygen or substituted nitrogen, provided that when E is substituted nitrogen, D is carbon, said nitrogen substituent being selected from the group consisting of hydrogen, $C_1$–$C_6$ alkyl and $C_2$–$C_6$ acyl; each $R_8$ may be $C_1$–$C_6$ alkyl, $C_1$–$C_6$ alkoxy, hydroxy or halogen, wherein the halogen may be chloro or fluoro; $R_9$ and $R_{10}$ may each be hydrogen or $C_1$–$C_6$ alkyl; and m may be the integer 0, 1, or 2; (iv) $C_1$–$C_6$ alkyl, $C_1$–$C_6$ haloalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$) alkyl-($C_3$–$C_6$)cycloalkyl, and halo ($C_3$–$C_6$)cycloalkyl, said halo groups being fluoro or chloro; and (v) the group represented by the following graphic formula II C:

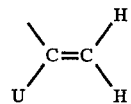

wherein U may be hydrogen or $C_1$–$C_4$ alkyl, and V may be selected from the unsubstituted, mono- and di-substituted members of the group consisting of naphthyl, phenyl, furanyl, and thienyl, wherein the substituents for each member of said group are $C_1$–$C_4$ alkyl, $C_1$–$C_4$ alkoxy, fluoro, or chloro; or (vi) B and B' taken together may form an unsubstituted, mono- or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene, cycloundecylidene, cyclododecylidene, saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1] nonan-9-ylidene, bicyclo[4.3.2]undecane, and saturated $C_7$–$C_{12}$ spiro-tricyclic hydrocarbon rings, e.g., tricyclo [2.2.1.0$^{2,6}$]heptylidene, tricyclo[5.3.1.1$^{2,6}$]dodecylidene, and tricyclo[3.3.1.1$^{3,7}$]decylidene, i.e., adamantylidene, wherein the fluoren-9-ylidene substituents may be selected from the group consisting of $C_1$–$C_4$ alkyl, $C_1$–$C_4$ alkoxy, fluoro and chloro.

Preferably, B and B' are each selected from the group consisting of: (i) unsubstituted, mono-, di- and tri-substituted phenyl; (ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl and carbazolyl, each of the phenyl and heterocyclic substituents being selected from the group consisting of morpholino, piperidino, $C_1$–$C_4$ alkyl, $C_1$–$C_4$ alkoxy and halogen, the halogen or (halo) group being fluoro or chloro; (iii) the groups represented by the graphic formula II A, wherein D is carbon and E is oxygen; each $R_8$ is $C_1$–$C_4$ alkyl, $C_1$–$C_4$ alkoxy, hydroxy or halogen, the halogen being chloro or fluoro; $R_9$ and $R_{10}$ are each hydrogen or $C_1$–$C_4$ alkyl; and m is the integer 0, 1 or 2; (iv) $C_1$–$C_4$ alkyl, $C_1$–$C_6$ alkoxy ($C_1$–$C_4$)alkyl and $C_3$–$C_6$ cycloalkyl; and (v) the group represented by graphic formula II C, wherein U is hydrogen or methyl, and V is phenyl or mono-substituted phenyl, the phenyl substituent being $C_1$–$C_4$ alkyl, $C_1$–$C_4$ alkoxy or fluoro; or (vi) B and B' taken together form an unsubstituted or mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon ring, and saturated $C_7$–$C_{10}$ spiro-tricyclic hydrocarbon rings.

More preferably, B and B' are each selected from the group consisting of: (i) unsubstituted, mono- and di-substituted phenyl; (ii) the unsubstituted, mono- and di-substituted heterocyclic aromatic groups pyridyl, benzofuran-2-yl, benzothien-2-yl, dibenzothienyl and dibenzofuranyl, each of the phenyl and heterocyclic substituents being selected from the group consisting of morpholino, piperidino, $C_1$–$C_2$ alkyl and $C_1$–$C_2$ alkoxy; and (iii) the groups represented by graphic formula II A, wherein D is carbon and E is oxygen; each $R_8$ is $C_1$–$C_2$ alkyl, $C_1$–$C_2$ alkoxy or fluoro; $R_9$ and $R_{10}$ are each hydrogen or $C_1$–$C_2$ alkyl; and m is the integer 0, 1 or 2; or (iv) B and B' taken together form fluoren-9-ylidene, bornylidene, norbornylidene, bicyclo[3.3.1]nonan-9-ylidene or adamantylidene. Most preferably, B and B' are each phenyl, methoxy substituted phenyl, morpholino substituted phenyl, dibenzofuran-2-yl, or 2,3-dihydrobenzofuran-5-yl.

Compounds represented by graphic formula I may be prepared by the following steps. Benzophenones represented by graphic formula V and VA are either purchased or prepared by Friedel-Crafts methods using an appropriately substituted or unsubstituted benzoyl chloride of graphic formula IV and a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

The compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent potential phenyl substituents.

REACTION A

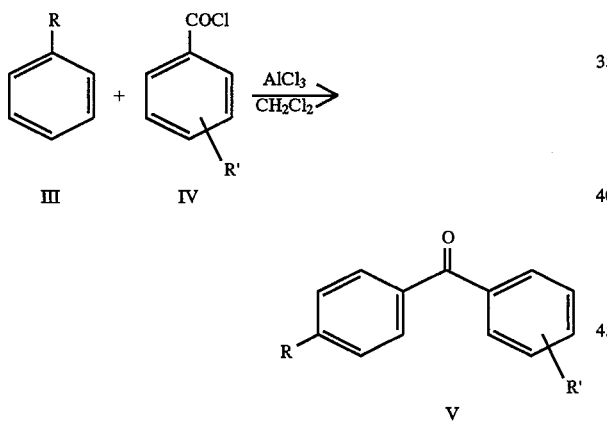

In Reaction B, the substituted or unsubstituted ketone represented by graphic formula VA, in which B and B' may represent groups other than substituted or unsubstituted phenyl, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or for example, from ketones prepared via reaction of an acyl halide with a substituted or unsubstituted benzene, naphthalene, or heteroaromatic compound. Propargyl alcohols having B or B' groups represented by graphic formula II C may be prepared by the methods described in U.S. Pat. No. 5,274,132, column 2, lines 40 to 68.

REACTION B

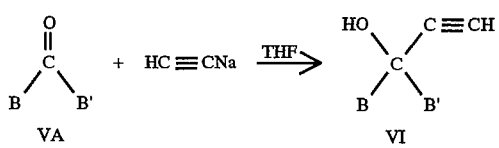

Naphthols represented by graphic formulae VIII and XIII, used in the preparation of naphthopyrans of graphic formula I, may be prepared as described in Reaction C or D. In Reaction C, 1,4-dihydroxy-2-naphthoic acid, represented by graphic formula VII, is reacted with an alkyl halide, e.g., methyl iodide, in the presence of ethyldiisopropyl amine in a suitable solvent such as anhydrous dimethylformamide (DMF), to form the corresponding methyl-1,4-dihydroxy-2-naphthoate, which is represented by graphic formula VIII. This reaction is further described in *The Journal of Organic Chemistry*, 46(17), 1981, page 3477.

REACTION C

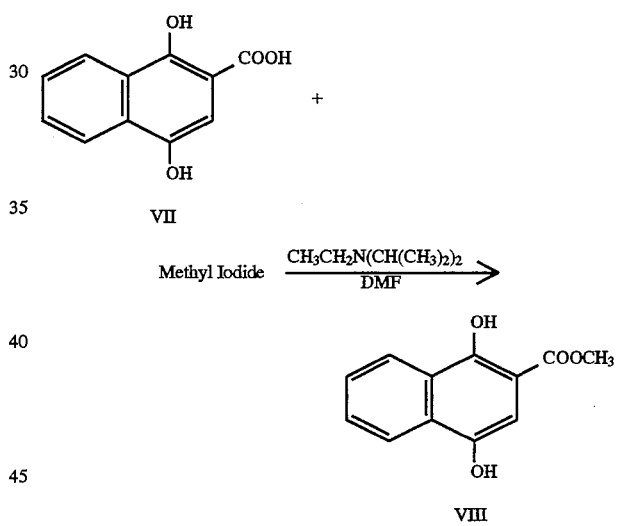

In Reaction D, a substituted or unsubstituted acetophenone, benzophenone, or benzaldehyde represented by graphic formula IX is reacted with dimethyl succinate (graphic formula X) in the presence of a base such as sodium hydride or potassium t-butoxide in a suitable solvent such as toluene or THF to form the appropriate substituted monoester of an α-arylidene succinic acid, represented by graphic formula XI. Compound XI is heated with acetic anhydride and anhydrous sodium acetate to form the corresponding acetate derivative represented by the graphic formula XII. Compound XII is reacted with hydrochloric acid and an anhydrous alcohol such as anhydrous methanol to form the corresponding naphthol, represented by graphic formula XIII. Reaction D is further described in the text *Organic Reactions*, Vol. VI, Chapter 1, pages 1–73, John Wiley & Sons, Inc., New York.

REACTION D

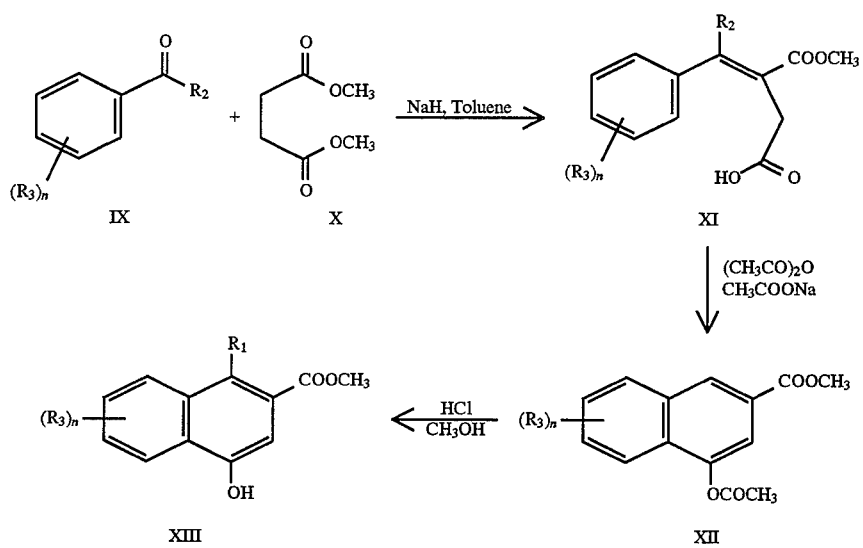

In Reaction E, a propargyl alcohol represented by graphic formula VI is coupled with a naphthol represented by graphic formula VIIIA (VIII further substituted with $(R_3)_n$) to form 6-hydroxy naphthopyrans represented by graphic formula XIV. The 6-hydroxy substituent of compounds represented by graphic formula XIV may be converted, for example to a 6-alkoxy group, by reaction with an alkyl halide, e.g., methyl iodide, ethyl iodide, benzyl bromide, etc., to form compounds represented by graphic formula XV. Compounds represented by graphic formula XV may be reduced, for example with lithium aluminum hydride (LAH) in an inert solvent such as THF to yield the 5-hydroxymethyl substituted compounds represented by graphic formula XVI. The 5-hydroxymethyl substituent of compounds represented by graphic formula XVI may be derivatized in a variety of ways. It can be converted to an alkoxymethyl by reacting compounds represented by graphic formula XVI with an alkyl halide such as methyl iodide, n-propyl bromide, benzyl bromide, etc., in the presence of a base such as potassium carbonate to produce compounds represented by graphic formula XVII. Alternatively the hydroxymethyl can be acylated with an acyl halide, e.g. acetyl chloride, benzoyl chloride, etc., to yield compounds represented by graphic formula XVIII. In a third example, the hydroxymethyl may be reacted with trimethylsilyl chloride, in the presence of an acid acceptor, e.g., triethyl amine, to produce trimethylsilyl ethers represented by compounds of graphic formula XIX.

REACTION E

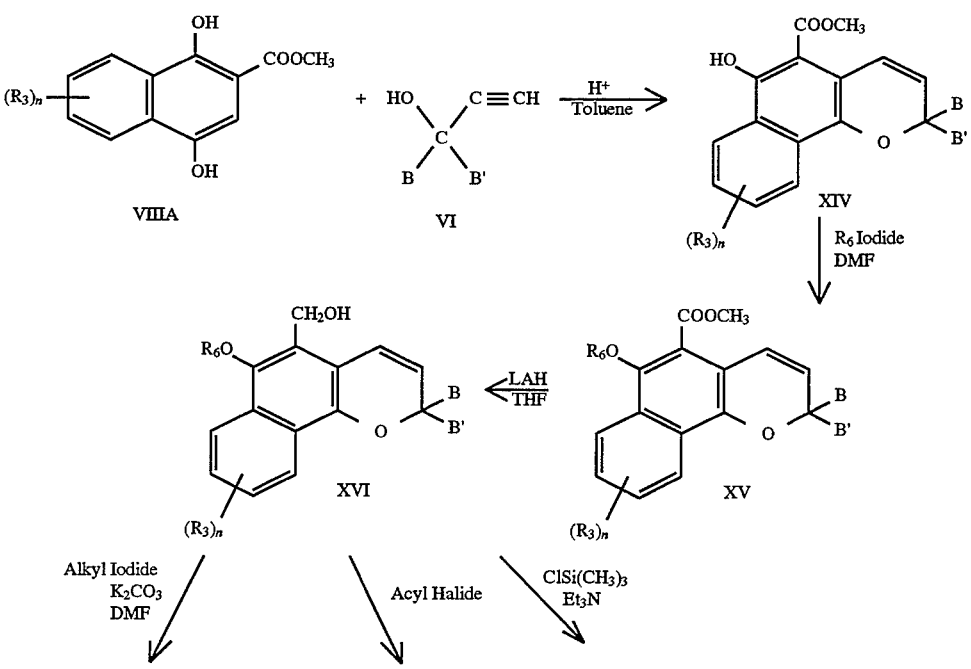

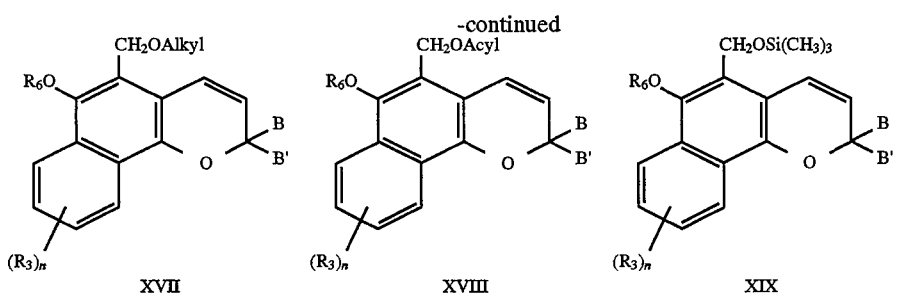

In Reaction F, a propargyl alcohol represented by graphic formula VI is coupled with a naphthol represented by graphic formula XIII to form 6-aryl, 6-alkyl, or 6-hydrogen bearing naphthopyran compounds represented by graphic formula XX. Compounds represented by graphic formula XX may be reduced, for example with lithium aluminum hydride (LAH) in an inert solvent such as THF to give 5-hydroxymethyl compounds represented by graphic formula XXI. The 5-hydroxymethyl substituent of compounds represented by graphic formula XXI may be derivatized in a variety of ways. It can be converted to a chloromethyl group by reacting compounds represented by graphic formula XXI with thionyl chloride to produce compounds represented by graphic formula XXII. The 5-chloromethyl of compounds represented by graphic formula XXII can be further derivatized using reactions known in the art, such as by reacting it with a primary, secondary, or heterocyclic amine, e.g. propyl amine, diethyl amine, morpholine, etc., to give 5-aminomethyl compounds represented by formula XXIII. Alternatively the hydroxymethyl group of compounds represented by graphic formula XXI can be reacted with an alkyl halide, e.g. methyl iodide, propyl iodide, benzyl bromide, etc., to yield compounds represented by graphic formula XXIV.

REACTION F

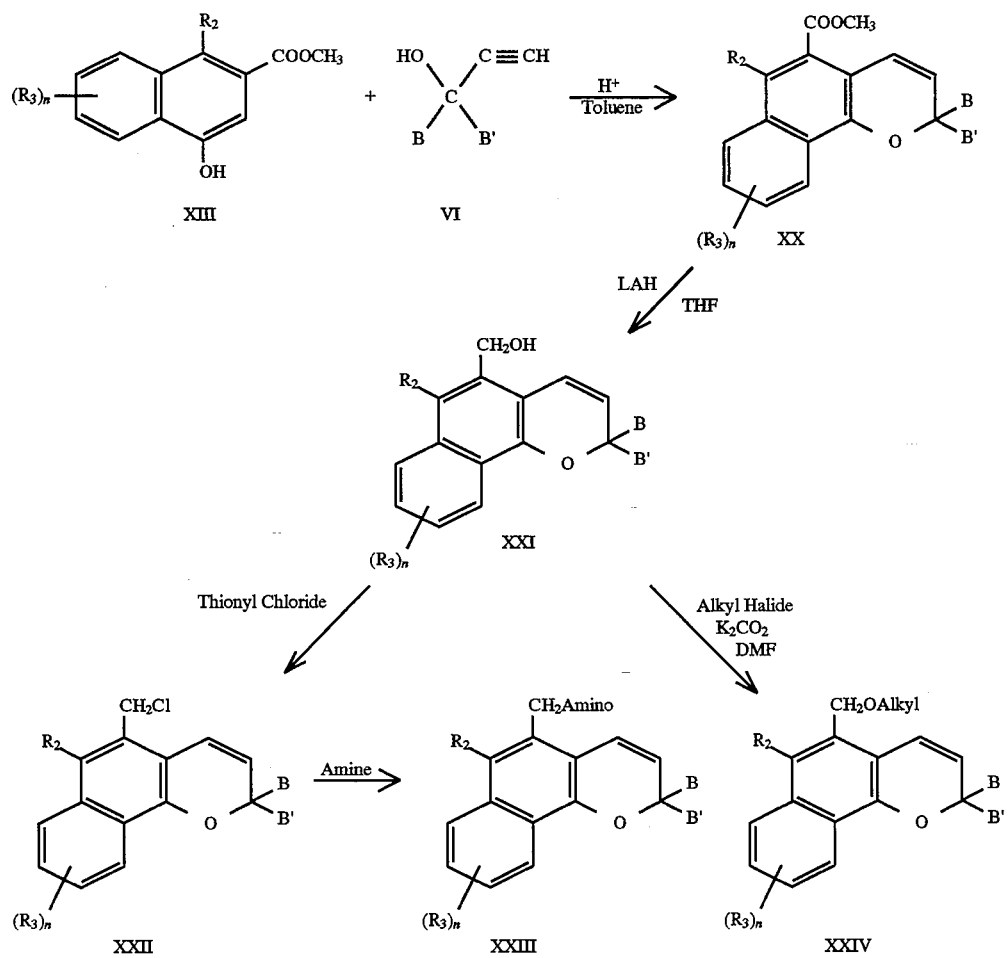

Compounds with an amide group substituted in the 5-position are prepared by the series of reactions found in Reaction G. Naphthols represented by graphic formula XIII are hydrolyzed to carboxynaphthols represented by formula XXV using potassium hydroxide dissolved in a mixture of water and alcohol. The free hydroxy substituent of compounds of graphic formula XXV is protected by reaction with acetyl chloride to yield acetoxy substituted compounds of graphic formula XXVI. The carboxy substituent of compounds of graphic formula XXVI is converted to an acid chloride by reaction with thionyl chloride to yield compounds of graphic formula XXVII. The acid chloride of compounds of graphic formula XXVII is converted to an amide group by reaction with a primary, secondary or heterocyclic amine, e.g. propyl amine, diethyl amine, morpholine, piperidine, etc., to give compounds of graphic formula XXVIII. The acetoxy substituent of compounds of graphic formula XXVIII is deprotected by reaction with methanol in the presence of HCl to yield the naphthols of graphic formula XXIX. Pyrans containing a 5-amide group represented by graphic formula XXX are prepared by reacting a naphthol of graphic formula XXIX with a propargyl alcohol of graphic formula VI.

REACTION G

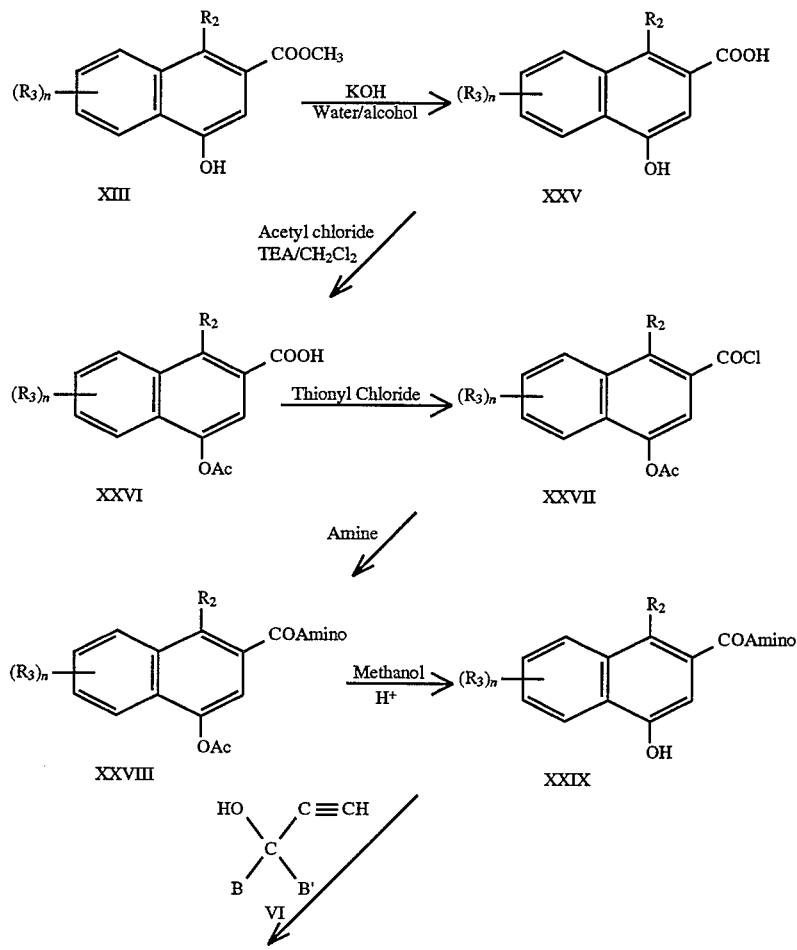

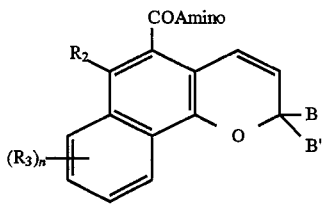

XXX

Compounds represented by graphic formula I may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from yellow to red/purple.

Examples of contemplated naphthopyrans within the scope of the invention are the following of:

(a) 2,2-bis(4-methoxyphenyl )-5-hydroxymethyl-6-methyl-9-methoxy-2H-naphtho[1,2-b]pyran;

(b) 2,2-bis(4-methoxyphenyl)-5-hydroxymethyl-6-phenyl-2H -naphtho[1,2-b]pyran;

(c) 2,2-bis (4-methoxyphenyl)-5-acetoxymethyl-6-phenyl-2H -naphtho[1,2 -b]pyran;

(d) 2-(4-methoxyphenyl)-2-(2,3-dihydrobenzofuran-5-yl)-5-piperidinocarbonyl-6-methyl-9-methoxy-2H-naphtho [1,2 -b]pyran;

(e) 2,2-bis(4-methoxyphenyl)-5-hydroxymethyl-6-methoxy-2H-naphtho[1,2-b]pyran;

(f) 2,2-diphenyl-5-methoxymethyl-6-methoxy-2H -naphtho [1,2-b]pyran;

(g) 2,2-spiroadamantylene-5-acetoxymethyl-6-methoxy-2H -naphtho[1,2-b]pyran;

(h) 2,2-bis(4-methoxyphenyl)-5-trimethylsilyloxymethyl-6-methoxy-2H -naphtho[1,2 -b]pyran;

(i) 2-(4-methoxyphenyl)-2-t-butyl-5-methoxymethyl-6-phenyl-9-methoxy-2H-naphtho[1,2-b]pyran; and (j) 2-(4-methoxyphenyl)-2-(2,3-dihydrobenzofuran-5-yl)-5-chloromethyl-6-methyl-9-methoxy-2H-naphtho[1,2-b] pyran.

It is contemplated that the organic photochromic naphthopyrans of graphic formula I be used in combination with other appropriate complementary organic photochromic materials so that together they produce a near neutral gray or brown color shade when the plastic lens containing such photochromic materials are exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than ophthalmic lenses.

The novel naphthopyran compounds of the present invention, such as those heretofore described, may be used alone or in combination with complementary photochromic compounds, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which compounds or mixtures of compounds color when activated to an appropriate hue.

A first group of complementary organic photochromic substances contemplated for use with the organic photochromic naphthopyrans of the present invention are those having an activated absorption maximum within the visible range of greater than 570 nanometers, e.g., between about greater than 570 to 700 nanometers. These materials typically exhibit a blue, blueish-green, or blueish-purple color when exposed to ultraviolet light in an appropriate solvent or matrix. Many of such compounds are described in the open literature. For example, spiro(indoline)naphthoxazines have been described, among others, in U.S. Pat. Nos. 3,562,172; 3,578,602; 4,215,010; and 4,342,668; spiro(indoline) naphthoxazines having certain substituents on the 8' and 9' positions of the naphthoxazine portion of the molecule are described in U.S. Pat. No. 5,405,958; spiro(indoline) pyridobenzoxazines are described in U.S. Pat. No. 4,637, 698; spiro(benzindoline)pyridobenzoxazines and spiro (benzindoline)naphthoxazines are described in U.S. Pat. No. 4,931,219; spiro(benzindoline)naphthopyrans are described in Japanese Patent Publication 62/195383; spiro(indoline) benzoxazines are described in U.S. Pat. No. 4,816,584; spiro(indoline)benzopyrans, spiro(indoline)naphthopyrans, and spiro(indoline)quinopyrans are described, for example, in U.S. Pat. No. 4,880,667; and benzopyrans and naphthopyrans having a nitrogen-containing substituent in the 2-position of the pyran ring are described in U.S. Pat. No. 4,818,096. Spiro(indoline)pyrans are also described in the text, Techniques in Chemistry, Volume III, "Photochromism," Chapter 3, Glenn H. Brown, Editor, John Wiley and Sons, Inc., New York, 1971.

A second group of complementary organic photochromic substances contemplated for use with the organic photochromic naphthopyrans of the present invention are those having at least one absorption maximum within the visible range of between about 400 and less than 500 nanometers. These materials typically exhibit a yellow-orange color when exposed to ultraviolet light in an appropriate solvent or matrix. Such compounds include certain chromenes, i.e., benzopyrans and naphthopyrans. Many of such chromenes are described in the open literature, e.g., U.S. Pat. Nos. 3,567,605; 4,826,977; and 5,066,818. Other examples of complementary benzopyrans and naphthopyrans that may be used with the naphthopyrans of the present invention include: those having a spiro adamantane group at the position alpha to the oxygen atom of the pyran ring, which are described in U.S. Pat. No. 4,826,977; 2H -naphtho-[1, 2-b]pyran compounds having certain substitutents at the number 5 and 6 carbon atoms of the naphtho portion of the naphthopyran and at the 2 position of the pyran which are the subject of co-pending U.S. patent application Ser. No. 08/164,187, filed Dec. 9, 1993; 3H-naphtho[2,1-b]pyrans having at least one ortho-substituted phenyl substituent at the 3-position of the pyran ring which are described in U.S. Pat. No. 5,066,818; 3H-naphtho[2,1-b]pyran compounds having certain substituents at the number 8 carbon atom and certain substituents at the number 7 or 9 carbon atom, all substituents being on the naphtho portion of the naphthopyran, which are the subject of co-pending U.S. patent application Ser. No. 08/080,246, filed Jun. 21, 1993; 3H-naphtho[2,1-b]pyrans substituted at the 3 position of the pyran ring with (i) an aryl substituent and (ii) a phenyl substituent having a 5- or 6-member heterocyclic ring fused at the number 3 and 4 carbon atoms of the phenyl substituent are described in U.S. Pat. No 5,384,077; diaryl-3H-naphtho[2,1-b]pyran compounds having a substituted or unsubstituted, 5 or 6 member heterocyclic ring fused to the g, i, or 1 side of the naphthopyran which are the subject of co-pending U.S. patent application Ser. No.08/225,022 filed Apr. 8, 1994; naphthopyran compounds substituted at the number 8 carbon atom on the naphtho portion of the naphthopyran ring, with for example, a methoxy group which are the subject of U.S. Pat. No. 5,238,931; naphthopyran compounds, examples of which are 3-aryl-3-arylalkenyl naphthopyrans, which are described in U.S. Pat. No. 5,274,132; and naphtho[2,1-b]pyrans substituted at the number five carbon atom with, for example, an acetoxy group, which are the subject of U.S. Pat. No. 5,244,602.

A third group of complementary organic photochromic substances contemplated for use with the organic photochromic naphthopyrans of the present invention are those having an absorption maximum within the visible range of between about 400 to about 500 nanometers and another absorption maximum within the visible range of between about 500 to about 700 nanometers. These materials typically exhibit color(s) ranging from yellow to purple and yellow/brown to purple/gray when exposed to ultraviolet light in an appropriate solvent or matrix. Examples of these compounds include certain substituted 2H-phenanthro[4,3-b]pyrans; substituted 3H -phenanthro[1,2-b]pyrans; and benzopyran compounds, such as those having substituents at the 2-position of the pyran ring and a substituted or unsubstituted heterocyclic ring, such as a benzothieno or benzofurano ring fused to the benz portion of the benzopyran. Such later described compounds are the subject of co-pending U.S. patent application Ser. Nos. 08/286,039 filed Aug. 4, 1994 and U.S. Pat. No. 5,411,679.

Photochromic articles of the present invention may contain one photochromic compound or a mixture of photochromic compounds, as desired or required. Individual photochromic compounds or mixtures of photochromic compounds may be used to attain certain activated colors such as neutral grays or browns.

The compounds of the present invention (hereinafter also referred to and included as a second group photochromic compound) may be used also in combination with the organic photochromic substances of the first complementary group of photochromic compounds described herein, i.e., those that color to colors blue, blueish-green, or blueish-purple or with other organic photochromic substances in the aforesaid second group of photochromic compounds. Either members of the first or second group of photochromic compounds or mixtures of such compounds may be combined with or used in conjunction with the third group described herein that exhibit colors ranging from yellow to purple and yellow/brown to purple/gray.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): $x=0.260$ to $0.400$, $y=0.280$ to $0.400$ following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied. When mixtures of the aforedescribed organic photochromic complementary groups are used, the weight ratio of such materials, i.e., (first to second), (second to third), and (naphthopyran of the present invention to other second group compounds) will vary from about 1:3 to about 3:1, between about 0.75:1 and about 2:1. The combination of the first, second, and third described organic photochromic complementary groups may have a weight ratio that will vary from about 1:3:1 to 3:1:3.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, and alkoxylated polyhydric alcohol acrylate monomers such as ethoxylated trimethylol propane triacrylate monomers; polymers, i.e., homopolymers and copolymers, of polyfunctional, i.e., mono-, di-, tri-, tetra, or multi-functional, acrylate and/or methacrylate monomers, polyacrylates, polymethacrylates, poly( $C_1$-$C_{12}$ alkyl methacrylates) such as poly(methyl methacrylate), polyoxy (alkylene methacrylates) such as poly(ethylene glycol bis methacrylates), poly(alkoxylated phenol methacrylates) such as poly(ethoxylated bisphenol A dimethacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. No. 4,360,653 and 4,994,208; and copolymers with aliphatic urethanes, the terminal portion of which contain allyl or acrylyl functional groups as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile. More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66.

The present invention is more particularly described in the following examples which are intended as illustrative only, since numerous modifications and variations therein will be apparent to those skilled in the art.

EXAMPLE 1

STEP 1

4,4'-Dimethoxybenzophenone (0.27 mole) was dissolved in a reaction flask containing 200 ml of anhydrous tetrahydrofuran saturated with acetylene and stirred at room temperature. An 18 weight percent suspension of sodium acetylide in xylene/mineral oil (0.3 mole of sodium acetylide) was added to the reaction flask and the mixture was stirred. After stirring 16 hours at room temperature under a nitrogen atmosphere, the contents of the reaction flask mixture was added to a 5 weight percent aqueous hydrochloric acid and ice mixture. The resulting mixture was extracted with diethyl ether. The organic layer was separated, washed, and dried over anhydrous sodium sulfate. The solvents, diethyl ether and tetrahydrofuran, were removed under vacuum to yield an oily product containing 1,1-bis(4-methoxyphenyl)-2-propyn-1-ol, which was not purified further but used directly in the next step.

STEP 2

1,1-Bis(4-methoxyphenyl)-2-propyn-1-ol (about 0.025 mole) from Step 1 and methyl, 4-hydroxy-6-methoxy-1-methyl-2-naphthoate (5 g, 0.022 mole) were added to a reaction flask containing 200 ml of toluene and stirred. A catalytic amount of p-toluene-sulfonic acid (about 100 milligrams) was added, and the mixture was stirred for 4 hours. Afterwards, the reaction mixture was poured into a 10 weight percent sodium hydroxide solution. The organic layer was separated, washed with water, and dried over anhydrous sodium sulfate. The remaining solvent, toluene, was removed under vacuum. The resulting oil was purified using a silica gel column and a 1:3 mixture of chloroform-:hexane as the eluant. The photochromic fractions were combined and the eluent was removed under vacuum. The resulting product was induced to crystallize from hexane. The recovered product had a melting point of 132°–133° C. A nuclear magnetic resonance (NMR) spectrum showed the product to have a structure consistent with 2,2-bis(4-methoxyphenyl)-5-methoxycarbonyl-6-methyl-9-methoxy-2H-naphtho[1,2-b]pyran.

STEP 3

2,2-Bis(4-methoxyphenyl)-5-methoxycarbonyl-6-methyl-9-methoxy-[2H]-naphtho[1,2-b]pyran (1.7 g, 0.0034 mole) from Step 2 was dissolved in a reaction flask containing 200 ml of tetrahydrofuran and stirred. Lithium aluminum hydride (0.13 g, 0.0034 mole) was carefully added and the mixture was stirred for 2 hours at room temperature. 2-Propanol was added followed by the addition of a 5 weight percent aqueous hydrochloric acid solution. The resulting mixture was extracted with two 100 ml portions of methylene chloride. The organic extracts were combined and dried over magnesium sulfate. The solvent, methylene chloride, was removed under vacuum. The product was induced to crystallize from diethyl ether and the crystals were collected by suction filtration. The recovered product, 1.0 g, had a melting point of 125°–127° C. A nuclear magnetic resonance (NMR) spectrum showed the product to have a structure consistent with 2,2-bis(4-methoxyphenyl)-5-hydroxymethyl-6-methyl-9-methoxy-2H-naphtho[1,2-b]pyran.

EXAMPLE 2

STEP 1

Potassium t-butoxide (75 grams(g), 0.75 mole) was added to a reaction flask containing 200 milliliters (ml) of toluene. The resulting slurry was heated to reflux temperature under a nitrogen atmosphere while a mixture of benzophenone (91 g, 0.5 mole), dimethyl succinate (90 g, 0.62 mole) and toluene (100 g) was added over a period of 30 minutes. After the addition, the resulting pasty mixture was maintained at reflux temperature for two hours and then cooled to room temperature. About 400 ml of water was added and the mixture was stirred for 30 minutes. The aqueous layer was separated, acidified with dilute hydrochloric acid, and extracted with 200 ml of toluene. The solvent was removed under vacuum yielding a viscous oil that later solidified, which contained the product, 4,4-diphenyl-3-methoxycarbonyl-3-butenoic acid. This material was not purified further but was used directly in the next step.

STEP 2

The product of Step 1 was dissolved in a reaction flask containing 200 ml of toluene. Acetic anhydride (100 g) and anhydrous sodium acetate (15 g) were added to the reaction flask and the mixture was refluxed for 17 hours. The resulting mixture was cooled to room temperature and the solvent was removed under vacuum. Methylene chloride (200 ml) was added to the reaction flask containing the resulting residue. Water (200 ml) was added to the reaction flask followed by the slow addition of solid sodium carbonate until the evolution of carbon dioxide ceased. The methylene chloride layer was separated, washed with water, and the solvent was removed under vacuum to yield a viscous oil containing 1-acetoxy-3-methoxycarbonyl-4-phenylnaphthalene.

STEP 3

Methanol (400 ml) was added to the reaction flask containing 1-acetoxy-3-methoxycarbonyl-4-phenylnaphthalene from Step 2. Hydrochloric acid, concentrated (2 ml) was added to the reaction flask and the resulting mixture was heated to reflux temperature. After 4 hours, the mixture was cooled to room temperature, the solvent was removed under vacuum, and the resulting crystals were collected by suction filtration. The collected crystals were washed with methanol and air dried. The recovered product, 100 g, had a melting point of 174°–176° C. A nuclear magnetic resonance (NMR) spectrum showed the product to have a structure consistent with 4-phenyl-3-methoxycarbonyl-1-naphthol.

STEP 4

4-Phenyl-3-methoxycarbonyl-1-naphthol (2 g) from Step 3 and 1,1-bis(4-methoxyphenyl)-2-propyn-1-ol (2 g) from Step 1 of Example 1 were added to a reaction flask containing 100 ml of toluene and stirred. The resulting mixture was heated to 40° C. and a catalytic amount (a few drops) of dodecyl benzenesulfonic acid was added, i.e., an amount sufficient to produce a deep red color in the mixture. After 3 hours of stirring at 40° C., the mixture was cooled and washed with water. The organic layer was separated, and the solvent, toluene was removed under vacuum. The resulting oil was purified using a silica gel column and a 2:1 hexane-:ethyl acetate mixture as the eluant. The photochromic fractions were collected and the solvent was removed under vacuum. The resulting product (2.0 g) was crystallized from a hexane-ether mixture and collected by suction filtration as off-white crystals. The recovered product had a melting point of 168°–169° C. A nuclear magnetic resonance (NMR) spectrum showed the product to have a structure consistent with 2,2-bis(4-methoxyphenyl)-5-methoxycarbonyl-6-phenyl-2H-naphtho[1,2-b]pyran.

STEP 5

2,2-Bis(4-methoxyphenyl)-5-methoxycarbonyl-6-phenyl-2H-naphtho[1,2-b]pyran (10.0 g, 0.02 mole) from Step 4 was dissolved in a reaction flask containing 300 ml of tetrahydrofuran. Lithium aluminum hydride (1.2 g, 0.032 mole) was carefully added to the stirred solution and the mixture heated to 40° C. for 2-½ hours. After cooling to room temperature, 2-propanol was added followed by the addition of a 5 weight percent aqueous hydrochloric acid solution. The resulting mixture was extracted with three 100 ml portions of diethyl ether. The organic extracts were combined and dried over magnesium sulfate. The solvent, diethyl ether, was removed under vacuum. The resulting residue was induced to crystallize from diethyl ether and the crystals were collected by suction filtration. Three grams of the desired product was recovered. A nuclear magnetic resonance (NMR) spectrum showed the product to have a structure consistent with 2,2-bis(4-methoxyphenyl)-5-hydroxymethyl-6-phenyl-2H-naphtho[1,2-b]pyran.

EXAMPLE 3

2,2-Bis(4-methoxyphenyl)-5-hydroxymethyl-6-phenyl-2H-naphtho[1,2-b]pyran (2.0 g, 0.004 mole) from Step 4 of Example 2, was dissolved in a reaction flask containing 200 ml of methylene chloride and 1.2 equivalents of triethyl amine. Acetyl chloride (0.37 g, 0.0048 mole) was added to the stirred mixture which was heated to reflux temperature for 4 hours. After cooling to room temperature, diethyl ether was added and triethylamine hydrochloride, a byproduct, was removed by filtration. The resulting product was purified on a silica gel column using chloroform as the eluant. The photochromic fractions were collected and the solvent was removed under vacuum. The recovered product, 0.2 g, was induced to crystallize from diethyl ether. A nuclear magnetic resonance (NMR) spectrum showed the product to have a structure consistent with 2,2-bis(4 -methoxyphenyl) -5-acetoxymethyl-6-phenyl-2H-naphtho[1,2-b]pyran.

STEP 1

3-methoxycarbonyl-4-methyl-7-methoxy-1-naphthol (12 g) was added to a reaction flask containing potassium hydroxide (25 g), water (250 ml) and ethanol (50 ml). The mixture was heated on a steam bath for six hours, cooled to room temperature, and poured into an excess of cold dilute (approximately 5 weight percent) aqueous hydrochloric acid. The resulting solid product was removed by suction filtration and dried to yield 11 g of the desired product, 3-carboxy-4-methyl-7-methoxy-1-naphthol.

STEP 2

3-carboxy-4-methyl-7-methoxy-1-naphthol (11 g) from Step 1 was added to a reaction flask containing 100 ml of methylene chloride. Triethyl amine (10 g, 0.1 mole) was added with stirring. The resulting exothermic reaction mixture was cooled in an ice bath. Acetyl chloride (4 g, 0.05 mole) was added dropwise while maintaining the temperature at 5° C. The mixture was stirred an additional 15 minutes at 5° C. and then warmed to room temperature where it was stirred an additional 15 minutes before pouring into an excess of cool dilute(approximately 5 weight percent) aqueous hydrochloric acid. The precipitated product was suction filtered from the two phase mixture, washed with fresh methylene chloride, and dried to yield 11 g of the desired product. A NMR spectrum showed the product to have a structure consistent with 1-acetoxy-3-carboxy-4-methyl-7-methoxynaphthalene.

STEP 3

1-acetoxy-3-carboxy-4-methyl-7-methoxynaphthalene (11 g) from Step 2 was added to a reaction flask containing 20 ml of thionyl chloride and the mixture was heated on a steam bath. After about 30 minutes, when HCl evolution was complete, the excess thionyl chloride was removed on a rotary evaporator to yield the acid chloride as a solid. The product, 1-acetoxy-3-chlorocarbonyl-4-methyl-7-methoxynaphthalene, was not further purified but was used directly in the next step.

STEP 4

One-half of the 1-acetoxy-3-chlorocarbonyl-4-methyl-7-methoxynaphthalene from Step 3 was added in small portions to a reaction flask containing a mixture of methylene chloride (50 ml), piperidine (4.25 g, 0.05 mole) and triethyl amine (5 g, 0.05 mole). After completing the addition, an excess of cool dilute (approximately 5 weight percent) aqueous hydrochloric acid was added and the resulting solution was mixed. The organic layer was separated, washed successively with water, dilute aqueous sodium carbonate, and water. The solvent, methylene chloride, was removed under vacuum to yield the desired product as an oil. A NMR spectrum showed the product to have a structure consistent with 1-acetoxy-3-piperidinocarbonyl-4-methyl-7-methoxynaphthalene.

STEP 5

A mixture (200 ml) of methanol and concentrated hydrochloric acid (2 ml) was added to a reaction flask containing 1-acetoxy-3-piperidinocarbonyl-4-methyl-7-methoxynaphthalene from Step 4. The resulting reaction mixture was refluxed on a steam bath for 2 hours. Afterwards, the mixture was cooled to room temperature and poured into dilute aqueous hydrochloric acid. The resulting precipitate was suction filtered, washed with water, and dried to yield 4.8 g of the desired product as tan crystals. A NMR spectrum showed the product to have a structure consistent with 3-piperidinocarbonyl-4-methyl-7-methoxy-1-naphthol.

STEP 6

3-piperidinocarbonyl-4-methyl-7-methoxy-1-naphthol (2.5 g) from Step 5 and 1-(2,3-dihydrobenzofur-5-yl)-1-(4-methoxyphenyl)-2-propyn-1-ol (2.5 g) were added to a reaction flask containing 100 ml of toluene and stirred. The stirred mixture was heated to 50° C. and a few drops of dodecyl benzenesulfonic acid were added (an amount sufficient to produce a deep red color). After two hours, the reaction mixture was cooled to room temperature and water was added. The organic layer was washed with water and the solvent was removed on a rotary evaporator. The resulting oil was purified using a silica gel column and a 1:1 hexane-:ethyl acetate mixture as the eluant. The photochromic fractions were combined, concentrated and induced to crystallize from a small amount of a diethyl ether:hexane mixture. The desired product was recovered by suction filtration and dried to yield 2.6 g of crystals having a melting point of 201°–203° C. A NMR spectrum showed the product to have a structure consistent with 2-(4-methoxyphenyl)-2-(2,3-dihydrobenzofuran-5-yl)-5-piperidinocarbonyl-6-methyl-9-methoxy-2H-naphtho[1,2-b]pyran.

EXAMPLE 5

PART A

Testing was done with the photochromic naphthopyrans of the Examples incorporated into polymeric samples by the following method. The quantity of naphthopyran calculated

23 to yield a 1.5 times $10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The naphthopyran was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven set to increase the temperature from 40° C. to 95° C. over a 5 hour interval, hold the temperature at 95° C. for 3 hours and then lower it to 60° C. for at least 2 hours before the end of the curing cycle. After the mold was opened, the polymer sheet was cut using a diamond blade saw into 2 inch (5.1 centimeters) test squares.

Part B

The photochromic test squares prepared in Part A were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 75° F. (23.9° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. A collimated beam of light from a tungsten lamp was passed through the square at a small angle normal to the square. After passing through the square, the light from the tungsten lamp was directed through a photopic filter attached to a detector. The photopic filter passes wavelengths such that the detector mimics the response of the human eye. The output signals from the detector(s) were processed by a radiometer.

Change in optical density ($\Delta$OD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula $\Delta$ OD=log(100/%Ta) where %Ta is the percent transmittance in the activated state and the logarithm is to the base 10.

The $\Delta$ OD/Min, which represents the sensitivity of the photochromic compound's response to UV light, was measured over the first five (5) seconds of UV exposure, then expressed on a per minute basis. The saturation optical density (OD) was taken under identical conditions as the $\Delta$ OD/Min, except UV exposure was continued for 20 minutes for the examples in Table 1. The lambda max reported in Table 1 is the wavelength in the visible spectrum at which the maximum absorption of the activated (colored) form of the photochromic compound in a diethylene glycol bis(allyl carbonate) composition occurs. The Bleach Rate (T ½) is the time interval in seconds for the absorbance of the activated form of the naphthopyran in the test squares to reach one half the highest absorbance at room temperature (75° F.,

24

23.9° C.) after removal of the source of activating light. Results for the Compounds of the Examples are tabulated in Table 1.

TABLE 1

| EXAMPLE COMPOUNDS | LAMBDA MAX (VISIBLE) | $\Delta$OD/MIN SENSITIVITY | $\Delta$OD@ SATURATION | Bleach (T½) |
|---|---|---|---|---|
| 1 | 520 | 0.38 | 0.42 | 303 sec |
| 2 | 506 | 0.32 | 0.26 | 149 sec |
| 3 | 508 | 0.33 | 0.25 | 109 sec |
| 4 | 535 | 0.34 | 0.65 | >800 sec |

The results of Table 1 show that the bleach rate of 2H-naphtho[1,2-b]pyrans is dramatically effected by the nature of the 5-position substituent. For example, Compounds 1 through 3 have an acceptable bleach rate, i.e., fade rate, while Compound 4 fades much slower. All 4 of the Example Compounds have a high OD at saturation, i.e., activated intensity, and a high coloration rate, i.e., sensitivity.

Although the present invention has been described with reference to the specific details of particular embodiments thereof, it is not intended that such details be regarded as limitations upon the scope of the invention except as and to the extent that they are included in the accompanying claims.

We claim:

1. A naphthopyran compound represented by the following graphic formula:

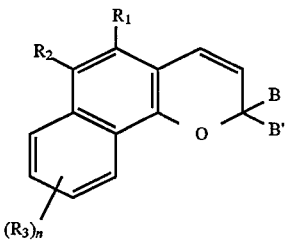

wherein, (a) $R_1$ is selected from the group consisting of —$CH_2X$ and —C(O)Y, wherein X is halogen, hydroxy, benzoyloxy, $C_1$–$C_6$ alkoxy, $C_2$–$C_6$ acyloxy, amino, $C_1$–$C_6$ mono-alkylamino, $C_1$–$C_6$ dialkylamino, morpholino, piperidino, 1-indolinyl, pyrrolidyl, trimethylsilyloxy, or the group, —OCH($R_{11}$)Z, Y is the group, —OCH($R_{11}$)Z, or an unsubstituted, monosubstituted, or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl, wherein Z is —CN, —$CF_3$, halogen, —C(O)$R_{12}$, or —COOR$_{12}$, $R_{11}$ and $R_{12}$ are hydrogen or $C_1$–$C_6$ alkyl; said heterocyclic ring substituents being selected from $C_1$–$C_6$ alkyl and $C_1$–$C_6$ alkoxy, and said halogen being chloro or fluoro;

(b) $R_2$ and each $R_3$ are hydrogen, $C_1$–$C_6$ alkyl, $C_3$–$C_7$ cycloalkyl, unsubstituted, mono-, di-, or tri-substituted phenyl, the group, —OR$_6$, wherein $R_6$ is hydrogen, ($C_1$–$C_6$)alkyl, phenyl($C_1$–$C_3$)alkyl, mono-substituted phenyl($C_1$–$C_3$)alkyl, ($C_1$–$C_6$)alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ haloalkyl, allyl, the group, —CH($R_7$)W, wherein W is —CN, —$CF_3$, halogen, —C(O)R$_7$, or —COOR$_7$, wherein R$_7$ is hydrogen, C$_1$–C$_6$ alkyl, or (C$_1$–C$_6$)alkoxy(C$_2$–C$_4$)alkyl, or R$_6$ is the group, —C(O)T, wherein T is hydrogen, C$_1$–C$_6$ alkyl, C$_1$–C$_6$ alkoxy, the substituted or unsubstituted aryl groups phenyl or naphthyl, phenoxy, C$_1$–C$_6$ mono- or di-alkyl substituted phenoxy, C$_1$–C$_6$ mono-or di-alkoxy substituted phenoxy, each of said phenyl or naphthyl substituents being C$_1$–C$_6$ alkyl, C$_1$–C$_6$ alkoxy or halogen, each of said halogen or halo substituents being chloro or fluoro and n is selected from the integers 0, 1, 2, and 3; and (c) B and B' are each selected from the group consisting of:
(i) the unsubstituted, mono-, di-, and tri-substituted aryl groups phenyl and naphthyl;
(ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl, and carbazolyl, said aryl and heterocyclic substituents being selected from the group consisting of hydroxy, amino, C$_1$–C$_6$ monoalkylamino, C$_1$–C$_6$ dialkylamino, morpholino, piperidino, 1-indolinyl, pyrrolidyl, 1-imidazolidyl, 2-imidazolin-1-yl, 2-pyrazolidyl, pyrazolinyl, 1-piperazinyl, C$_1$–C$_6$ alkyl, C$_1$–C$_6$ haloalkyl, C$_1$–C$_6$ alkoxy, mono(C$_1$–C$_6$) alkoxy(C$_1$–C$_4$)alkyl, acryloxy, methacryloxy, and halogen, said halogen or (halo) group being fluoro or chloro;
(iii) the groups represented by the following graphic formulae:

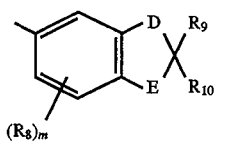 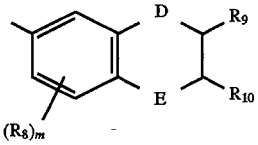

wherein D is carbon or oxygen and E is oxygen or substituted nitrogen, provided that when E is substituted nitrogen, D is carbon, said nitrogen substituent being selected from the group consisting of hydrogen, C$_1$–C$_6$ alkyl, and C$_2$–C$_6$ acyl; each R$_8$ is C$_1$–C$_6$ alkyl, C$_1$–C$_6$ alkoxy, hydroxy, chloro or fluoro; R$_9$ and R$_{10}$ are each hydrogen or C$_1$–C$_6$ alkyl; and m is the integer 0, 1, or 2;
(iv) C$_1$–C$_6$ alkyl, C$_1$–C$_6$ haloalkyl, C$_1$–C$_6$ alkoxy (C$_1$–C$_4$)alkyl, C$_3$–C$_6$ cycloalkyl, mono(C$_1$–C$_6$) alkoxy(C$_3$–C$_6$)cycloalkyl, mono(C$_1$–C$_6$)alkyl (C$_3$–C$_6$)cycloalkyl, and halo(C$_3$–C$_6$)cycloalkyl, said halo groups being fluoro or chloro; and
(v) the group represented by the following graphic formula:

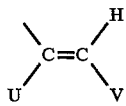

wherein U is hydrogen or C$_1$–C$_4$ alkyl, and V is selected from the unsubstituted, mono-, and di-substituted members of the group consisting of naphthyl, phenyl, furanyl, and thienyl, wherein the substituents for each member of said group are C$_1$–C$_4$ alkyl, C$_1$–C$_4$ alkoxy, fluoro, or chloro; or
(vi) B and B' taken together form an unsubstituted, mono-, or di-substituted fluoren-9-ylidene or a member selected from the group consisting of saturated C$_3$–C$_{12}$ spiro-monocyclic hydrocarbon rings, saturated C$_7$–C$_{12}$ spiro-bicyclic hydrocarbon rings, and saturated C$_7$–C$_{12}$ spiro-tricyclic hydrocarbon rings, said fluoren-9-ylidene substituents being selected from the group consisting of C$_2$–C$_4$ alkyl, C$_1$–C$_4$ alkoxy, fluoro and chloro.

2. The naphthopyran of claim 1 wherein:
(a) R$_1$ is selected from the group consisting of —CH$_2$X and —C(O)Y, wherein X is hydroxy, C$_1$–C$_4$ alkoxy, or C$_2$–C$_4$ acyloxy, Y is the group, —OCH(R$_{11}$)Z, or an unsubstituted or mono-substituted heterocyclic ring selected from the group consisting of 1-indolinyl, morpholino, piperidino, and 1-pyrrolidyl, wherein Z is —CN, —C(O)R$_{12}$, or —COOR$_{12}$, R$_{11}$ and R$_{12}$ are hydrogen or C$_1$–C$_4$ alkyl; said heterocyclic ring substituents being selected from C$_1$–C$_4$ alkyl and C$_1$–C$_4$ alkoxy;
(b) R$_2$ and each R$_3$ are hydrogen, C$_1$–C$_4$ alkyl, unsubstituted, mono-, di-, or tri-substituted phenyl, the group, —OR$_6$, wherein R$_6$ is C$_1$–C$_4$ alkyl or the group, CH(R$_7$)W, wherein W is —COOR$_7$, and R$_7$ is hydrogen or C$_1$–C$_4$ alkyl, said phenyl substituents being C$_1$–C$_4$ alkyl, C$_1$–C$_4$ alkoxy or fluoro and n is selected from the integers 0, 1, and 2; and
(c) B and B' are each selected from the group consisting of:
(i) unsubstituted, mono-, di-, and tri-substituted phenyl;
(ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl, and carbazolyl, each of said phenyl and heterocyclic substituents being selected from the group consisting of morpholino, piperidino, C$_1$–C$_4$ alkyl, C$_1$–C$_4$ alkoxy, and halogen, said halogen or (halo) group being fluoro or chloro;
(iii) the groups represented by the following graphic formula:

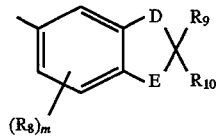

wherein D is carbon and E is oxygen; each R$_8$ is C$_1$–C$_4$ alkyl, C$_1$–C$_4$ alkoxy, hydroxy, or halogen, said halogen being chloro or fluoro; R$_9$ and R$_{10}$ are each hydrogen or C$_1$–C$_4$ alkyl; and m is the integer 0, 1, or 2;
(iv) C$_1$–C$_4$ alkyl, C$_1$–C$_6$ alkoxy(C$_1$–C$_4$)alkyl, and C$_3$–C$_6$ cycloalkyl; and
(v) the group represented by the following graphic formula:

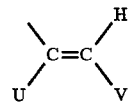

wherein U is hydrogen or methyl, and V is phenyl or mono-substituted phenyl, said phenyl substituent being C$_1$–C$_4$ alkyl, C$_1$–C$_4$ alkoxy, or fluoro; or
(vi) B and B' taken together form an unsubstituted or mono-substituted fluoren-9-ylidene or a member selected from the group consisting of saturated C$_3$–C$_8$ spiro-monocyclic hydrocarbon rings, saturated C$_7$–C$_{10}$ spiro-bicyclic hydrocarbon rings, and saturated C$_7$–C$_{10}$ spiro-tricyclic hydrocarbon rings.

3. The naphthopyran of claim 2 wherein:

(a) $R_1$ is the group, —$CH_2X$, or —$C(O)Y$, wherein X is hydroxy, $C_1$–$C_4$ alkoxy, or $C_2$–$C_4$ acyloxy and Y is an unsubstituted or mono-substituted heterocyclic ring selected from the group consisting of 1-indolinyl, morpholino, and piperidino;

(b) $R_2$ and each $R_3$ are hydrogen, $C_1$–$C_2$ alkyl, unsubstituted, mono-, di-, or tri-substituted phenyl, the group, —$OR_6$, wherein $R_6$ is $C_1$–$C_2$ alkyl or the group, —$CH(R_7)W$, wherein W is —$COOR_7$, and $R_7$ is $C_1$–$C_2$ alkyl, said phenyl substituents being $C_1$–$C_2$ alkyl, $C_1$–$C_2$ alkoxy or fluoro, and n is selected from the integers 0, 1, and 2; and (c) B and B' are each selected from the group consisting of:

(i) unsubstituted, mono-, and di-substituted phenyl;

(ii) the unsubstituted, mono- and di-substituted heterocyclic aromatic groups pyridyl, benzofuran-2-yl, benzothien-2-yl, dibenzothienyl, and dibenzofuranyl, each of said phenyl and heterocyclic substituents being selected from the group consisting of morpholino, piperidino, $C_1$–$C_2$ alkyl, and $C_1$–$C_2$ alkoxy; and (iii) the groups represented by the following graphic formula:

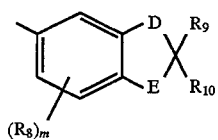

wherein D is carbon and E is oxygen; each $R_8$ is $C_1$–$C_2$ alkyl, $C_1$–$C_2$ alkoxy or fluoro; $R_9$ and $R_{10}$ are each hydrogen or $C_1$–$C_2$ alkyl; and m is the integer 0, 1, or 2; or (iv) B and B' taken together form fluoren-9-ylidene, bornylidene, norbornylidene, bicyclo[3.3.1]nonan-9-ylidene or adamantylidene.

4. The naphthopyran of claim 3 wherein $R_1$ is hydroxymethyl, acetoxymethyl, morpholinocarbonyl, or piperidinocarbonyl; $R_2$ and each $R_3$ are hydrogen, phenyl, methoxy, or methyl; and B and B' are each phenyl, methoxy substituted phenyl, morpholino substituted phenyl, dibenzofuran-2-yl, or 2,3-dihydrobenzofuran-5-yl.

5. A naphthopyran compound selected from the group consisting of:

(a) 2,2-bis (4-methoxyphenyl)-5-hydroxymethyl-6-methyl-9-methoxy-2H -naphtho[1,2-b]pyran;

(b) 2,2-bis (4-methoxyphenyl)-5-hydroxymethyl-6-phenyl-2H-naphtho[1,2-b]pyran;

(c) 2,2-bis (4-methoxyphenyl)-5-acetoxymethyl-6-phenyl-2H -naphtho[1,2-b]pyran;

(d) 2-(4-methoxyphenyl)-2-(2,3-dihydrobenzofuran-5-yl)-5-piperidinocarbonyl-6-methyl-9-methoxy-2H-naphtho[1,2-b]pyran;

(e) 2,2-bis(4-methoxyphenyl)-5-hydroxymethyl-6-methoxy-2H-naphtho[1,2-b]pyran;

(f) 2,2-diphenyl-5-methoxymethyl-6-methoxy-2H-naphtho[1,2-b]pyran;

(g) 2,2-spiroadamantylene-5-acetoxymethyl-6-methoxy-2H-naphtho[1,2-b]pyran;

(h) 2,2-bis(4-methoxyphenyl)-5-trimethylsilyloxymethyl-6-methoxy-2H-naphtho[1,2-b]pyran;

(i) 2-(4-methoxyphenyl)-2-t-butyl-5-methoxymethyl-6-phenyl-9-methoxy-2H-naphtho[1,2-b]pyran; and (j) 2-(4-methoxyphenyl)-2-(2,3-dihydrobenzofuran-5-yl)-5-chloromethyl-6-methyl-9-methoxy-2H-naphtho[1,2-b]pyran.

6. A photochromic article comprising a polymeric organic host material and a photochromic amount of a naphthopyran compound of claim 1.

7. The photochromic article of claim 6 wherein the polymeric organic host material is selected from the group consisting of polyacrylates, polymethacrylates, poly($C_1$–$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

8. A photochromic article comprising a polymeric organic host material and a photochromic amount of a naphthopyran compound of claim 2.

9. The photochromic article of claim 8 wherein the polymeric organic host material is selected from the group consisting of polyacrylates, polymethacrylates, poly($C_1$–$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

10. The photochromic article of claim 9 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

11. The photochromic article of claim 10 wherein the photochromic compound is present in an amount of from about 0.05 to 1.0 milligram per square centimeter of organic host material surface to which the photochromic substance (s) is incorporated or applied.

12. The photochromic article of claim 11 wherein the article is a lens.

13. A photochromic article comprising a photochromic amount of the naphthopyran compound of claim 3 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

14. A photochromic article comprising a photochromic amount of the naphthopyran compound of claim 4 and a polymeric organic host material selected from the group consisting of poly(methyl methacrylate), poly(ethylene glycol bis methacrylate), poly(ethoxylated hisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of polyacrylates, polymethacrylates, poly($C_1$–$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

17. The photochromic article of claim 15 wherein the organic photochromic compound (b) is selected from the group consisting of:

(a) organic photochromic substances having at least one absorption maximum in the visible range of between 400 and less than 500 nanometers;

(b) organic photochromic substances having an absorption maximum within the visible range of between about 400 and 500 nanometers and an absorption maximum within the visible range of between 500 and 700 nanometers; and (c) organic photochromic substances having an activated absorption maxima in the visible range of greater than 570 nanometers; and (d) mixtures of said organic photochromic substances.

18. The photochromic article of claim 17 wherein the organic photochromic compound (b) is an organic photochromic substances having an activated absorption maxima in the visible range of greater than 570 nanometers.

19. The photochromic article of claim 16 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

20. The photochromic article of claim 17 wherein the organic photochromic compound (b) is selected from the group consisting of spiro(indoline)naphthoxazines, spiro (indoline)-pyridobenzoxazines, spiro(benzindoline) pyridobenzoxazines, spiro(benzindoline)naphthoxazines, spiro(benzindoline)naphthopyrans, spiro(indoline) benzoxazines, spiro(indoline)benzopyrans, spiro(indoline) naphthopyrans, spiro(indoline)quinopyrans, spiro(indoline) pyrans, 3H -naphtho[2,1-b]pyrans, 2H-phenanthro[4,3-b] pyrans; 3H -phenanthro[1,2-b]pyrans; benzopyran compounds and mixtures of such photochromic substances.

21. The naphthopyran of claim 2 wherein:

(a) $R_1$ is the group —C(O)Y, wherein Y is the group, —OCH($R_{11}$)Z, wherein $R_{11}$ is hydrogen and Z is —COOR$_{12}$, wherein $R_{12}$ is $C_1$–$C_4$ alkyl;

(b) $R_2$ is hydrogen;

(c) $R_3$ is $C_1$–$C_4$ alkyl, n is 1; and (d) B and B' are each phenyl.

22. The naphthopyran of claim 21 wherein $R_3$ is $C_1$–$C_2$ alkyl.

23. The naphthopyran of claim 22 wherein $R_3$ is methyl.

24. A photochromic article comprising a polymeric organic host material and a photochromic amount of a naphthopyran compound of claim 21.

25. A photochromic article comprising a polymeric organic host material and a photochromic amount of a naphthopyran compound of claim 22.

* * * * *